United States Patent
Lorant

(10) Patent No.: US 9,445,985 B2
(45) Date of Patent: Sep. 20, 2016

(54) COSMETIC COMPOSITION COMPRISING SILICA AEROGEL PARTICLES AND AN EMULSIFYING SILICONE ELASTOMER

(71) Applicant: L'OREAL, Paris (FR)

(72) Inventor: Raluca Lorant, Thiais (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/375,955

(22) PCT Filed: Feb. 5, 2013

(86) PCT No.: PCT/EP2013/052247
§ 371 (c)(1),
(2) Date: Jul. 31, 2014

(87) PCT Pub. No.: WO2013/117549
PCT Pub. Date: Aug. 15, 2013

(65) Prior Publication Data
US 2014/0370063 A1    Dec. 18, 2014

Related U.S. Application Data

(60) Provisional application No. 61/600,763, filed on Feb. 20, 2012.

(30) Foreign Application Priority Data

Feb. 6, 2012    (FR) .................................... 12 51077

(51) Int. Cl.
| | |
|---|---|
| *A61K 8/894* | (2006.01) |
| *A61K 8/02* | (2006.01) |
| *A61K 8/25* | (2006.01) |
| *A61K 8/06* | (2006.01) |
| *A61Q 19/00* | (2006.01) |
| *A61Q 19/08* | (2006.01) |

(52) U.S. Cl.
CPC ............ *A61K 8/894* (2013.01); *A61K 8/0279* (2013.01); *A61K 8/064* (2013.01); *A61K 8/25* (2013.01); *A61Q 19/00* (2013.01); *A61Q 19/007* (2013.01); *A61Q 19/08* (2013.01); *A61K 2800/20* (2013.01); *A61K 2800/31* (2013.01); *A61K 2800/651* (2013.01)

(58) Field of Classification Search
CPC ..................... A61K 2800/20; A61K 2800/31; A61K 2800/651; A61K 8/0279; A61K 8/064; A61K 8/25; A61K 8/894; A61Q 19/00; A61Q 19/007; A61Q 19/08
See application file for complete search history.

(56) References Cited

U.S. PATENT DOCUMENTS

2007/0274932 A1    11/2007    Suginaka et al.

FOREIGN PATENT DOCUMENTS

| WO | WO-2012/030993 A2 | 3/2012 |
|---|---|---|
| WO | WO-2012/085856 A2 | 6/2012 |

OTHER PUBLICATIONS

Dow Corning: "Dow Corning VM-2270 Aerogel Fine Particles", Internet Citation, Apr. 2009, pp. 1-5.
International Search Report and Written Opinion issued Oct. 21, 2013 in PCT/EP2013/052247.

*Primary Examiner* — Aradhana Sasan
(74) *Attorney, Agent, or Firm* — Polsinelli PC

(57) ABSTRACT

A subject matter of the present invention is a composition for topical application comprising hydrophobic silica aerogel particles and at least one emulsifying silicone elastomer. Another subject matter of the invention is a method for the cosmetic treatment of keratinous substances which consists in applying, to the keratinous substances, a composition as defined above, and also the use of this composition in the cosmetic or dermatological field and in particular for caring for, protecting and/or making up the skin of the body or face or for caring for the hair. The composition of the invention makes it possible to improve the sensory properties of cosmetic compositions provided in the anhydrous or emulsified form by making possible more complete absorption, without a greasy or unpleasant residual film on the skin.

18 Claims, No Drawings

COSMETIC COMPOSITION COMPRISING SILICA AEROGEL PARTICLES AND AN EMULSIFYING SILICONE ELASTOMER

CROSS REFERENCE TO RELATED APPLICATIONS

This application is a National Phase filing under 35 U.S.C. §371 of PCT/EP2013/052247 filed on Feb. 5, 2013; and this application claims priority to Application No. 1251077 filed in France on Feb. 6, 2012; and this application claims the benefit of U.S. Provisional Application No. 61/600,763 filed on Feb. 20, 2012; the entire contents of each application is hereby incorporated by reference.

The present patent application relates to a composition for topical application comprising hydrophobic silica aerogel particles and at least one emulsifying silicone elastomer, and to the use of said composition in the cosmetic and dermatological fields, in particular for caring for or treating keratinous substances.

In the cosmetic field and more particularly in the field of the care of the skin and makeup, it is commonplace to use formulation architectures having an oily continuous phase, whether in the anhydrous form or in the emulsified form of water-in-oil type.

These formulation forms exhibit the advantage of being good vehicles for active agents or sunscreens or also good carriers for makeup compositions by virtue of their film-forming effect and of the good resistance of the film formed on the skin.

On the other hand, these film-forming compositions exhibit disadvantages, in particular of a sensory nature and with regard to comfort of use. This is because the residual film is often perceived as greasy and gives a feeling of skin which does not breathe.

In order to overcome these disadvantages, provision has been made to prepare emulsions of water-in-oil type having a high water content which are stabilized by emulsifying silicone elastomers which exhibit the advantage of emulsifying high contents of water.

Thus, the patent EP 1 068 851 describes the use of such an emulsifier to stabilize emulsions of water-in-oil type comprising at least 70% of aqueous phase. However, the compositions according to this patent, although effectively introducing a degree of lightness on application by virtue of the high content of aqueous phase, do not introduce the known benefits of water-in-oil emulsions, such as, for example, nutrition and comfort for dry skin.

Document WO2012/030993 relates to a method for treating wounds, comprising applying to a wound on a subject a formulation comprising a first reactive reinforcing component and a second cross-linking component, wherein said cross-linking component catalyzes an in situ cross-linking of the reactive reinforcing component, such that a film is formed on the wound, thereby treating the wound. This document discloses in the examples compositions that were effective in removing the film.

The need thus remains for well-balanced and comfortable compositions which introduce deeply felt effects of protected and nourished skin without leaving an excessive residual film.

The Applicant Company has found, surprisingly, that the combination of a silica aerogel with an emulsifying silicone elastomer makes it possible to obtain compositions exhibiting good film-forming properties while retaining good cosmetic properties, such as a pleasant feeling on the skin.

Thus, a subject matter of the present invention is a composition for topical application comprising hydrophobic silica aerogel particles and at least one emulsifying silicone elastomer.

As the composition of the invention is intended for topical application to the skin or superficial body growths, it comprises a physiologically acceptable medium, that is to say a medium compatible with all keratinous substances, such as the skin, nails, mucous membranes and keratinous fibers (such as the hair or eyelashes).

The composition of the invention makes it possible to improve the sensory properties of cosmetic compositions provided in the anhydrous or emulsified form by making possible more complete absorption, without a greasy or unpleasant residual film on the skin.

Another subject matter of the invention is a method for the cosmetic treatment of keratinous substances which consists in applying, to the keratinous substances, a composition as defined above.

Another subject matter of the invention is the use of said composition in the cosmetic or dermatological field and in particular for caring for, protecting and/or making up the skin of the body or face or for caring for the hair.

In that which follows, the expression "at least one" is equivalent to "one or more" and, unless otherwise indicated, the limits of a range of values are included within this range.

Hydrophobic Silica Aerogels

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York, Academic Press, 1990.

The hydrophobic silica aerogel particles used in the present invention exhibit a specific surface per unit of weight ($S_W$) ranging from 500 to 1500 $m^2/g$, preferably from 600 to 1200 $m^2/g$ and better still from 600 to 800 $m^2/g$, and a size, expressed as the volume-average diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles used in the present invention exhibit a size, expressed as volume-average diameter (D[0.5]), ranging from 1 to 30 μm, preferably from 5 to 25 μm, better still from 5 to 20 μm and even better still from 5 to 15 μm.

The specific surface per unit of weight can be determined by the nitrogen absorption method, known as the BET (Brunauer-Emmett-Teller) method, described in The Journal of the American Chemical Society, Vol. 60, page 309, February 1938, which corresponds to international standard ISO 5794/1 (Appendix D). The BET specific surface corresponds to the total specific surface of the particles under consideration.

The sizes of the silica aerogel particles can be measured by static light scattering using a commercial particle size analyzer of MasterSizer 2000 type from Malvern. The data are processed on the basis of the Mie scattering theory. This theory, which is exact for isotropic particles, makes it possible to determine, in the case of nonspherical particles, an "effective" particle diameter. This theory is described in particular in the publication by Van de Hulst, H. C., "Light Scattering by Small Particles", Chapters 9 and 10, Wiley, New York, 1957.

According to an advantageous embodiment, the hydrophobic silica aerogel particles used in the present invention exhibit a specific surface per unit of weight ($S_W$) ranging from 600 to 800 m$^2$/g and a size, expressed as the volume-average diameter (D[0.5]), ranging from 5 to 20 μm and even better still from 5 to 15 μm.

The silica aerogel particles used in the present invention can advantageously exhibit a packed density (ρ) ranging from 0.04 g/cm$^3$ to 0.10 g/cm$^3$ and preferably from 0.05 g/cm$^3$ to 0.08 g/cm$^3$.

In the context of the present invention, this density, known as the packed density, can be assessed according to the following protocol:

40 g of powder are poured into a graduated measuring cylinder; the measuring cylinder is then placed on the Stav 2003 device from Stampf Volumeter; the measuring cylinder is subsequently subjected to a series of 2500 packing actions (this operation is repeated until the difference in volume between 2 consecutive tests is less than 2%); and then the final volume Vf of packed powder is measured directly on the measuring cylinder. The packed density is determined by the ratio w/Vf, in this instance 40/Vf (Vf being expressed in cm$^3$ and w in g).

According to one embodiment, the hydrophobic silica aerogel particles used in the present invention exhibit a specific surface per unit of volume $S_V$ ranging from 5 to 60 m$^2$/cm$^3$, preferably from 10 to 50 m$^2$/cm$^3$ and better still from 15 to 40 m$^2$/cm$^3$.

The specific surface per unit of volume is given by the relationship: $S_V=S_W\times\rho$; where ρ is the packed density, expressed in g/cm$^3$, and $S_W$ is the specific surface per unit of weight, expressed in m$^2$/g, as defined above.

Preferably, the hydrophobic silica aerogel particles according to the invention have an oil absorption capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method of determination of oil uptake of a powder described in the standard NF T 30-022. It corresponds to the amount of oil adsorbed onto the available surface of the powder and/or absorbed by the powder by measurement of the wet point, described below:

An amount w=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/w.

The aerogels used according to the present invention are hydrophobic silica aerogels, preferably silylated silica (INCI name: silica silylate) aerogels.

The term "hydrophobic silica" is understood to mean any silica, the surface of which is treated with silylating agents, for example with halogenated silanes, such as alkylchlorosilanes, siloxanes, in particular dimethylsiloxanes, such as hexamethyldisiloxane, or silazanes, so as to functionalize the OH groups with silyl groups Si—Rn, for example trimethylsilyl groups.

As regards the preparation of hydrophobic silica aerogel particles modified at the surface by silylation, reference may be made to the document U.S. Pat. No. 7,470,725.

Use will in particular be made of hydrophobic silica aerogel particles modified at the surface with trimethylsilyl groups (trimethylsiloxylated silica).

Mention may be made, as hydrophobic silica aerogels which can be used in the invention, for example, of the aerogel sold under the name VM-2260 (INCI name: Silica silylate) by Dow Corning, the particles of which exhibit an average size of approximately 1000 microns and a specific surface per unit of weight ranging from 600 to 800 m$^2$/g.

Mention may also be made of the aerogels sold by Cabot under the references Aerogel TLD 201, Aerogel OGD 201, Aerogel TLD 203, Enova® Aerogel MT 1100 and Enova Aerogel MT 1200.

Use will more particularly be made of the aerogel sold under the name VM-2270 (INCI name: Silica silylate) by Dow Corning, the particles of which exhibit an average size ranging from 5-15 microns and a specific surface per unit of weight ranging from 600 to 800 m$^2$/g.

The hydrophobic silica aerogel particles can be present in the composition according to the invention in a content as active material ranging from 0.1% to 15% by weight, preferably from 1% to 10% by weight, better still from 1% to 5% by weight and more preferably from 1% to 3% by weight, with respect to the total weight of the composition.

Emulsifying Silicone Elastomers

The term "silicone elastomer" is understood to mean a partially or completely crosslinked organopolysiloxane, which is a flexible and deformable material having viscoelastic properties. Its modulus of elasticity is such that this material withstands deformation and has a limited ability to extend and to contract. This material is capable of regaining its original shape after stretching.

The term "emulsifying silicone elastomer" is understood to mean a silicone elastomer comprising at least one hydrophilic chain, it being possible for this chain in particular to be oxyalkylenated or glycerolated.

According to a specific embodiment of the invention, the emulsifying silicone elastomer or elastomers can be chosen from polyoxyalkylenated silicone elastomers, polyglycerolated silicone elastomers and their mixtures.

Polyoxyalkylenated Silicone Elastomers

The polyoxyalkylenated silicone elastomer is a crosslinked organopolysiloxane which can be obtained by a crosslinking addition reaction of a diorganopolysiloxane comprising at least one hydrogen bonded to silicon and of a polyoxyalkylene having at least two ethylenically unsaturated groups.

Preferably, the polyoxyalkylenated crosslinked organopolysiloxane is obtained by a crosslinking addition reaction (A1) of a diorganopolysiloxane comprising at least two hydrogens each bonded to a silicon and (B1) of a polyoxyalkylene having at least two ethylenically unsaturated groups, in particular in the presence (C1) of a platinum catalyst, such as, for example, described in the U.S. Pat. No. 5,236,986 and U.S. Pat. No. 5,412,004.

In particular, the organopolysiloxane can be obtained by reaction of polyoxyalkylene (in particular a polyoxyethylene and/or polyoxypropylene) possessing dimethylvinylsiloxy ends and of a methylhydropolysiloxane possessing trimethylsiloxy ends, in the presence of a platinum catalyst.

The organic groups bonded to the silicon atoms of the compound (A1) can be alkyl groups having from 1 to 18 carbon atoms, such as methyl, ethyl, propyl, butyl, octyl, decyl, dodecyl (or lauryl), myristyl, cetyl or stearyl; substituted alkyl groups, such as 2-phenylethyl, 2-phenylpropyl or 3,3,3-trifluoropropyl; aryl groups, such as phenyl, tolyl or xylyl; substituted aryl groups, such as phenylethyl; and substituted monovalent hydrocarbon groups, such as an epoxy group, a carboxylate ester group or a mercapto group.

The compound (A1) can thus be chosen from methylhydropolysiloxanes possessing trimethylsiloxy ends, dimethylsiloxane/methylhydrosiloxane copolymers possessing trimethylsiloxy ends, cyclic dimethylsiloxane/methylhydrosiloxane copolymers, or dimethylsiloxane/methylhydrosiloxane/laurylmethylsiloxane copolymers possessing trimethylsiloxy ends.

The compound (C1) is the catalyst of the crosslinking reaction and is in particular chloroplatinic acid, chloroplatinic acid/olefin complexes, chloroplatinic acid/alkenylsiloxane complexes, chloroplatinic acid/diketone complexes, platinum black and platinum-on-support.

Advantageously, the polyoxyalkylenated silicone elastomers can be formed from divinyl compounds, in particular polyoxyalkylenes having at least two vinyl groups, which react with Si—H bonds of a polysiloxane.

The polyoxyalkylenated silicone elastomer according to the invention is preferably mixed with at least one hydrocarbon oil and/or one silicone oil in order to form a gel. In these gels, the polyoxyalkylenated elastomer can be in the form of nonspherical particles.

Polyoxyalkylenated elastomers are described in particular in the U.S. Pat. No. 5,236,986, U.S. Pat. No. 5,412,004, U.S. Pat. No. 5,837,793 and U.S. Pat. No. 5,811,487.

Use may be made, as polyoxyalkylenated silicone elastomer, of those sold under the names KSG-21, KSG-20, KSG-30, KSG-31, KSG-32, KSG-33, KSG-210, KSG-310, KSG-320, KSG-330, KSG-340, X-226146, KSG-380Z and KSG-320Z by Shin-Etsu, and DC9010 and DC9011 by Dow Corning.

According to a preferred embodiment, use will be made of the polyoxyalkylenated silicone elastomer sold under the name KSG-210 by Shin-Etsu.

Polyglycerolated Silicone Elastomers

The polyglycerolated silicone elastomer is a crosslinked organopolysiloxane elastomer which can be obtained by a crosslinking addition reaction of a diorganopolysiloxane comprising at least one hydrogen bonded to silicon and of polyglycerolated compounds having ethylenically unsaturated groups, in particular in the presence of a platinum catalyst.

Preferably, the crosslinked organopolysiloxane elastomer is obtained by a crosslinking addition reaction (A) of a diorganopolysiloxane comprising at least two hydrogens each bonded to a silicon and (B) of glycerolated compounds having at least two ethylenically unsaturated groups, in particular in the presence (C) of a platinum catalyst.

In particular, the organopolysiloxane can be obtained by reaction of a polyglycerolated compound possessing dimethylvinylsiloxy ends and of a methylhydropolysiloxane possessing trimethylsilyloxy ends, in the presence of a platinum catalyst.

The compound (A) is the base reactant for the formation of an organopolysiloxane elastomer and the crosslinking takes place by an addition reaction of the compound (A) with the compound (B) in the presence of the catalyst (C).

The compound (A) is in particular an organopolysiloxane having at least 2 hydrogen atoms bonded to separate silicon atoms in each molecule.

The compound (A) can exhibit any molecular structure, in particular a linear chain or branched chain structure or a cyclic structure.

The compound (A) can have a viscosity at 25° C. ranging from 1 to 50 000 centistokes, in particular in order to be satisfactorily miscible with the compound (B).

The organic groups bonded to the silicon atoms of the compound (A) can be alkyl groups having from 1 to 18 carbon atoms, such as methyl, ethyl, propyl, butyl, octyl, decyl, dodecyl (or lauryl), myristyl, cetyl or stearyl; substituted alkyl groups, such as 2-phenylethyl, 2-phenylpropyl or 3,3,3-trifluoropropyl; aryl groups, such as phenyl, tolyl or xylyl; substituted aryl groups, such as phenylethyl; and substituted monovalent hydrocarbon groups, such as an epoxy group, a carboxylate ester group or a mercapto group. Preferably, said organic group is chosen from the methyl, phenyl and lauryl groups.

The compound (A) can thus be chosen from methylhydropolysiloxanes possessing trimethylsiloxy ends, dimethylsiloxane/methylhydrosiloxane copolymers possessing trimethylsiloxy ends, cyclic dimethylsiloxane/methylhydrosiloxane copolymers, or dimethylsiloxane/methylhydrosiloxane/laurylmethylsiloxane copolymers possessing trimethylsiloxy ends.

The compound (B) can be a polyglycerolated compound corresponding to the following formula (B'):

$$C_mH_{2m-1}-O-[Gly]_n-C_mH_{2m-1} \quad (B')$$

in which m is an integer ranging from 2 to 6, n is an integer ranging from 2 to 200, preferably ranging from 2 to 100, preferably ranging from 2 to 50, preferably n ranging from 2 to 20, preferably ranging from 2 to 10 and preferentially ranging from 2 to 5, and in particular equal to 3; Gly denotes:

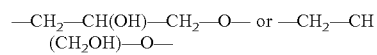

—CH$_2$—CH(OH)—CH$_2$—O— or —CH$_2$—CH(CH$_2$OH)—O—

Advantageously, the sum of the number of ethylene groups per molecule of the compound (B) and of the number of hydrogen atoms bonded to silicon atoms per molecule of the compound (A) is at least 4.

It is advantageous for the compound (A) to be added in an amount such that the molecular ratio of the total amount of hydrogen atoms bonded to silicon atoms in the compound (A) to the total amount of all the ethylenically unsaturated groups in the compound (B) is within the range from 1/1 to 20/1.

The compound (C) is the catalyst of the crosslinking reaction and is in particular chloroplatinic acid, chloroplatinic acid/olefin complexes, chloroplatinic acid/alkenylsiloxane complexes, chloroplatinic acid/diketone complexes, platinum black and platinum-on-support.

The catalyst (C) is preferably added from 0.1 to 1000 parts by weight, better still from 1 to 100 parts by weight, as platinum metal proper, per 1000 parts by weight of the total amount of the compounds (A) and (B).

The polyglycerolated silicone elastomer according to the invention is generally mixed with at least one hydrocarbon oil and/or one silicone oil in order to form a gel. In these gels, the polyglycerolated elastomer is often in the form of nonspherical particles.

Such elastomers are described in particular in the patent application WO 2004/024798. Use may be made, as polyglycerolated silicone elastomers, of those sold under the names KSG-710, KSG-810, KSG-820, KSG-830, KSG-840 and KSG-820Z by Shin-Etsu.

The emulsifying silicone elastomer or elastomers can be present in the composition of the invention in a content as active material ranging from 0.05% to 10% by weight, in particular from 0.5% to 10% by weight and preferably from 0.5% to 5% by weight, with respect to the total weight of said composition.

The composition according to the invention can be provided in various formulation forms conventionally used for topical applications and in particular in the form of dispersions of the serum type, of emulsions with a liquid or semiliquid consistency of the milk type, obtained by dispersion of a fatty phase in an aqueous phase (O/W) or vice versa (W/O), or of suspensions or emulsions with a soft, semisolid or solid consistency of the cream or gel type, or alternatively of multiple emulsions (W/O/W or O/W/O), of microemulsions, or of vesicular dispersions of ionic and/or nonionic type. These compositions are prepared according to the usual methods.

In addition, the compositions used according to the invention can be more or less fluid and can have the appearance of a gel, a white or colored cream, an ointment, a milk, a serum, a paste or a foam.

According to a specific embodiment, the composition according to the invention is provided in the form of an anhydrous composition.

According to another specific embodiment, the composition according to the invention is provided in the form of a water-in-oil emulsion comprising a continuous oily phase and an aqueous phase dispersed in said oily phase, or in the form of an oil-in-water emulsion comprising a continuous aqueous phase and an oily phase dispersed in said aqueous phase.

According to a preferred embodiment, the composition of the invention is provided in the form of an emulsion of water-in-oil type (inverse emulsion).

Within the meaning of the present invention, the term "anhydrous" is understood to mean a composition comprising a content of less than or equal to 1% by weight of water, preferably of less than or equal to 0.5% by weight, with respect to the total weight of said composition, indeed even devoid of water. If appropriate, such small amounts of water may in particular be introduced by ingredients of the composition, which may comprise residual amounts thereof.

Fatty Phase

According to a specific embodiment, the composition according to the invention comprises at least one fatty phase.

When the composition is provided in the form of an anhydrous composition, the proportion of the fatty phase can range, for example, from 30% to 99% by weight and preferably from 50% to 90% by weight, with respect to the total weight of the composition. When the composition is provided in the form of an emulsion, the proportion of the fatty phase can range, for example, from 1% to 80% by weight and preferably from 5% to 40% by weight, with respect to the total weight of the composition.

This indicated amount does not comprise the content of lipophilic surfactants.

Within the meaning of the invention, the fatty phase includes any fatty substance which is liquid at ambient temperature and atmospheric pressure, generally oils, or which is solid at ambient temperature and atmospheric pressure, such as waxes, or any pasty compound, which are present in said composition.

The fatty phase of the composition in accordance with the invention generally comprises at least one volatile or nonvolatile oil.

The term "oil" is understood to mean any fatty substance which is in liquid form at ambient temperature (25° C.) and at atmospheric pressure.

The volatile or nonvolatile oils can be hydrocarbon oils, in particular of animal or vegetable origin, synthetic oils, silicone oils, fluorinated oils or their mixtures.

Within the meaning of the present invention, the term "silicone oil" is understood to mean an oil comprising at least one silicon atom, and in particular at least one Si—O group.

The term "hydrocarbon oil" is understood to mean an oil mainly comprising hydrogen and carbon atoms and optionally oxygen, nitrogen, sulfur and/or phosphorus atoms.

Nonvolatile Oils

Within the meaning of the present invention, the term "nonvolatile oil" is understood to mean an oil having a vapor pressure of less than 0.13 Pa (0.01 mmHg).

The nonvolatile oils can be chosen in particular from nonvolatile hydrocarbon oils, if appropriate fluorinated, and/or nonvolatile silicone oils.

Mention may in particular be made, as nonvolatile hydrocarbon oil suitable for use in the invention, of:
hydrocarbon oils of animal origin,
hydrocarbon oils of vegetable origin, such as phytosteryl esters, such as phytosteryl oleate, phytosteryl isostearate and lauroyl/octyldodecyl/phytosteryl glutamate, for example sold under the name Eldew PS203 by Ajinomoto, triglycerides composed of fatty acid esters of glycerol, the fatty acids of which can have varied chain lengths from $C_4$ to $C_{24}$, it being possible for the latter to be linear or branched and saturated or unsaturated; these oils are in particular heptanoic or octanoic triglycerides, apricot kernel oil, wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkinseed oil, cucumber oil, blackcurrant oil, evening primrose oil, millet oil, barley oil, quinoa oil, rye oil, safflower oil, candlenut oil, passionflower oil or musk rose oil; shea butter; or alternatively caprylic/capric acid triglycerides, such as those sold by Stearineries Dubois or those sold under the names Miglyol 810®, 812® and 818® by Dynamit Nobel; or the refined vegetable perhydrosqualene sold under the name Fitoderm by Cognis;
hydrocarbon oils of mineral or synthetic origin, such as, for example:
synthetic ethers having from 10 to 40 carbon atoms,
linear or branched hydrocarbons of mineral or synthetic origin, such as liquid petroleum, polydecenes, hydrogenated polyisobutene, such as Parleam, squalane and their mixtures, in particular hydrogenated polyisobutene;
synthetic esters, such as oils of formula $R_1COOR_2$ in which $R_1$ represents the residue of a linear or branched fatty acid comprising from 1 to 40 carbon atoms and $R_2$ represents a hydrocarbon chain, in particular a branched hydrocarbon chain, comprising from 1 to 40 carbon atoms, provided that $R_1+R_2$ is $\geq 10$.

The esters can in particular be chosen from esters, in particular fatty acid esters, such as, for example:

dicaprylyl carbonate (Cetiol CC from Cognis), cetearyl octanoate, esters of isopropyl alcohol, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, such as isostearyl lactate, octyl hydroxystearate, diisopropyl adipate, heptanoates, in particular isostearyl heptanoate, octanoates, decanoates or ricinoleates of alcohols or polyalcohols, such as propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol di(2-ethylhexanoate) and their mixtures, benzoates of $C_{12}$ to $C_{15}$ alcohols, hexyl laurate, neopentanoic acid esters, such as isodecyl neopentanoate, isotridecyl neopentanoate, isostearyl neopentanoate or octyldodecyl neopentanoate, isononanoic acid esters, such as isononyl isononanoate, isotridecyl isononanoate or octyl isononanoate, or hydroxylated esters, such as isostearyl lactate or diisostearyl malate, polyol esters and pentaerythritol esters, such as dipentaerythrityl tetrahydroxystearate/tetraisostearate, esters of dimer diols and of dimer diacids, such as Lusplan DD-DA5® and Lusplan DD-DA7®, sold by Nippon Fine Chemical and described in patent application FR 03 02809, fatty alcohols which are liquid at ambient temperature, comprising a branched and/or unsaturated carbon chain having from 12 to 26 carbon atoms, such as 2-octyldodecanol, isostearyl alcohol, oleyl alcohol, 2-hexyldecanol, 2-butyloctanol and 2-undecylpentadecanol, higher fatty acids, such as oleic acid, linoleic acid, linolenic acid and their mixtures, and dialkyl carbonates, it being possible for the two alkyl chains to be identical or different, such as dicaprylyl carbonate, sold under the name Cetiol CC® by Cognis, nonvolatile silicone oils, such as, for example, nonvolatile polydimethylsiloxanes (PDMSs), polydimethylsiloxanes comprising alkyl or alkoxy groups which are pendent and/or at the ends of the silicone chain, which groups each have from 2 to 24 carbon atoms, phenyl silicones, such as phenyl trimethicones, phenyl dimethicones, phenyl(trimethylsiloxy)diphenylsiloxanes, diphenyl dimethicones, diphenyl(methyldiphenyl)trisiloxanes and (2-phenylethyl)trimethylsiloxysilicates, dimethicones or phenyl trimethicones with a viscosity of less than or equal to 100 cSt, and their mixtures; and their mixtures.

Volatile Oils

Within the meaning of the present invention, the term "volatile oil" is understood to mean an oil (or nonaqueous medium) which is capable of evaporating on contact with the skin in less than one hour, at ambient temperature and at atmospheric pressure. The volatile oil is a volatile cosmetic oil which is liquid at ambient temperature, having in particular a nonzero vapor pressure at ambient temperature and atmospheric pressure, especially having a vapor pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon oils can be chosen from hydrocarbon oils having from 8 to 16 carbon atoms, in particular branched $C_8$-$C_{16}$ alkanes (also known as isoparaffins), such as isododecane (also known as 2,2,4,4,6-pentamethylheptane), isodecane or isohexadecane, for example the oils sold under the Isopar® or Permethyl® trade names. Use may also be made, as volatile oils, of volatile silicones, such as, for example, volatile linear or cyclic silicone oils, in particular those having a viscosity 8 centistokes ($8\times10^{-6}$ m$^2$/s), and having in particular from 2 to 10 silicon atoms and especially from 2 to 7 silicon atoms, these silicones optionally comprising alkyl or alkoxy groups having from 1 to 10 carbon atoms. Mention may in particular be made, as volatile silicone oil which can be used in the invention, of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane and their mixtures.

Use may also be made of volatile fluorinated oils, such as nonafluoromethoxybutane or perfluoromethylcyclopentane, and their mixtures.

It is also possible to use a mixture of the oils mentioned above.

Within the meaning of the present invention, the term "pasty fatty substance" is understood to mean a lipophilic fatty compound which exhibits a reversible solid/liquid change in state, which exhibits, in the solid state, an anisotropic crystalline arrangement and which comprises, at a temperature of 23° C., a liquid fraction and a solid fraction.

In other words, the starting melting point of the pasty fatty substance can be less than 23° C. The liquid fraction of the pasty fatty substance, measured at 23° C., can represent from 9% to 97% by weight of the pasty fatty substance. This liquid fraction at 23° C. preferably represents between 15% and 85% and more preferably between 40% and 85% by weight.

Within the meaning of the invention, the melting point corresponds to the temperature of the most endothermic peak observed in thermal analysis (DSC) as described in the standard ISO 11357-3; 1999. The melting point of a pasty fatty substance can be measured using a differential scanning calorimeter (DSC), for example the calorimeter sold under the name MDSC 2920 by TA Instruments.

The measurement protocol is as follows:

A sample of 5 mg of pasty fatty substance placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C., at a heating rate of 5° C./minute.

During the second temperature rise, the variation in the difference in power absorbed by the empty crucible and by the crucible containing the sample of pasty fatty substance is measured as a function of the temperature. The melting point of the pasty fatty substance is the value of the temperature corresponding to the tip of the peak of the curve representing the variation in the difference in power absorbed as a function of the temperature.

The liquid fraction by weight of the pasty fatty substance at 23° C. is equal to the ratio of the enthalpy of fusion consumed at 23° C. to the enthalpy of fusion of the pasty fatty substance.

The enthalpy of fusion of the pasty fatty substance is the enthalpy consumed by the latter in order to pass from the solid state to the liquid state. The pasty fatty substance is said to be in the solid state when all of its mass is in crystalline solid form. The pasty fatty substance is said to be in the liquid state when all of its mass is in liquid form.

The enthalpy of fusion of the pasty fatty substance is equal to the area under the curve of the thermogram obtained using a differential scanning calorimeter (DSC), such as the calorimeter sold under the name MDSC 2920 by TA Instruments, with a temperature rise of 5° C. or 10° C. per minute, according to the standard ISO 11357-3:1999.

The enthalpy of fusion of the pasty fatty substance is the amount of energy required to make the pasty fatty substance change from the solid state to the liquid state. It is expressed in J/g.

The enthalpy of fusion consumed at 23° C. is the amount of energy absorbed by the sample to change from the solid state to the state which it exhibits at 23° C., consisting of a liquid fraction and a solid fraction.

The liquid fraction of the pasty fatty substance measured at 32° C. preferably represents from 30% to 100% by weight of the pasty fatty substance, preferably from 50% to 100%, more preferably from 60% to 100% by weight of the pasty fatty substance. When the liquid fraction of the pasty fatty substance measured at 32° C. is equal to 100%, the temperature of the end of the melting range of the pasty fatty substance is less than or equal to 32° C.

The liquid fraction of the pasty fatty substance measured at 32° C. is equal to the ratio of the enthalpy of fusion consumed at 32° C. to the enthalpy of fusion of the pasty fatty substance. The enthalpy of fusion consumed at 32° C. is calculated in the same way as the enthalpy of fusion consumed at 23° C.

The pasty fatty substance is preferably chosen from synthetic fatty substances and fatty substances of vegetable origin. A pasty fatty substance can be obtained by synthesis from starting materials of vegetable origin.

The pasty fatty substance is advantageously chosen from:
lanolin and its derivatives,
polyol ethers chosen from ethers of pentaerythritol and of polyalkylene glycol, ethers of fatty alcohol and of sugar, and their mixtures, the ether of pentaerythritol and of polyethylene glycol comprising 5 oxyethylene (5 OE) units (CTFA name: PEG-5 Pentaerythrityl Ether), the ether of pentaerythritol and of polypropylene glycol comprising 5 oxypropylene (5 OP) units (CTFA name: PPG-5 Pentaerythrityl Ether), and their mixtures, and more especially the PEG-5 Pentaerythrityl Ether, PPG-5 Pentaerythrityl Ether and soybean oil mixture, sold under the name Lanolide by Vevy, in which mixture the constituents are in a 46/46/8 ratio by weight: 46% PEG-5 Pentaerythrityl Ether, 46% PPG-5 Pentaerythrityl Ether and 8% soybean oil,
polymeric or nonpolymeric silicone compounds,
polymeric or nonpolymeric fluorinated compounds,
vinyl polymers, in particular:
olefin homopolymers and copolymers,
hydrogenated diene homopolymers and copolymers,
fat-soluble polyethers resulting from the polyetherification between one or more $C_2$-$C_{100}$ and preferably $C_2$-$C_{50}$ diols,
esters,
and/or their mixtures.

The pasty fatty substance is preferably a polymer, in particular a hydrocarbon polymer. Preference is given in particular, among the fat-soluble polyethers, to copolymers of ethylene oxide and/or of propylene oxide with long-chain $C_6$-$C_{30}$ alkylene oxides, more preferably such that the ratio by weight of the ethylene oxide and/or of the propylene oxide to the alkylene oxides in the copolymer is from 5:95 to 70:30. In this family, mention will in particular be made of copolymers such that the long-chain alkylene oxides are arranged in blocks having an average molecular weight of from 1000 to 10 000, for example a polyoxyethylene/polydodecyl glycol block copolymer, such as the ethers of dodecanediol (22 mol) and of polyethylene glycol (45 OE) sold under the brand name Elfacos ST9 by Akzo Nobel.

Preference is given in particular, among the esters, to:
esters of a glycerol oligomer, in particular diglycerol esters, especially condensates of adipic acid and of glycerol, for which a portion of the hydroxyl groups of the glycerols has reacted with a mixture of fatty acids, such as stearic acid, capric acid, isostearic acid and 12-hydroxystearic acid, such as in particular those sold under the brand name Softisan 649 by Sasol,
arachidyl propionate, sold under the brand name Waxenol 801 by Alzo,
phytosterol esters,
fatty acid triglycerides and their derivatives,
pentaerythritol esters,
esters of dimer diol and dimer diacid, if appropriate esterified on their free alcohol or acid functional group(s) by acid or alcohol radicals, in particular dimer dilinoleate esters; such esters can be chosen in particular from esters with the following INCI nomenclature: bis-behenyl/isostearyl/phytosteryl dimer dilinoleyl dimer dilinoleate (Plandool G), phytosteryl isostearyl dimer dilinoleate (Lusplan PI-DA or Lusplan PHY/IS-DA), phytosteryl/isostearyl/cetyl/stearyl/behenyl dimer dilinoleate (Plandool H or Plandool S), and their mixtures,
mango butter, such as that sold under the reference Lipex 203 by AarhusKarlshamn,
hydrogenated soybean oil, hydrogenated coconut oil, hydrogenated rapeseed oil or mixtures of hydrogenated vegetable oils, such as the soybean, coconut, palm and rapeseed hydrogenated vegetable oil mixture, for example the mixture sold under the reference Akogel® by AarhusKarlshamn (INCI name: Hydrogenated Vegetable Oil),
shea butter, in particular that having the INCI name Butyrospermum Parkii Butter, such as that sold under the reference Sheasoft® by AarhusKarlshamn,
cocoa butter, in particular that which is sold under the name CT Cocoa Butter Deodorized by Dutch Cocoa BV or that which is sold under the name Beurre De Cacao NCB HD703 758 by Barry Callebaut,
shorea butter, in particular that which is sold under the name Dub Shorea T by Stearinerie Dubois,
and their mixtures.

According to a preferred embodiment, the pasty fatty substance is chosen from shea butter, cocoa butter, shorea butter, a soybean, coconut, palm and rapeseed hydrogenated vegetable oil mixture, and their mixtures, and more particularly those referenced above.

The waxes under consideration in the context of the present invention are generally deformable or nondeformable solid lipophilic compounds at ambient temperature (25° C.) which exhibit a reversible solid/liquid change in state and which have a melting point of greater than or equal to 30° C. which can range up to 200° C. and in particular up to 120° C. On bringing one or more waxes in accordance with the invention to the liquid state (melting), it is possible to render it or them miscible with one or more oils and to form a macroscopically homogeneous mixture of wax(es) and oil(s) but, on bringing the temperature of said mixture back to ambient temperature, recrystallization of the wax(es) in the oil(s) of the mixture is obtained.

Within the meaning of the invention, the melting point corresponds to the temperature of the most endothermic peak observed in thermal analysis (DSC) as described in the standard ISO 11357-3; 1999. The melting point of the wax can be measured using a differential scanning calorimeter (DSC), for example the calorimeter sold under the name MDSC 2920 by TA Instruments.

The measurement protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and finally it is subjected to a second temperature rise ranging from −20° C. to 100° C., at a heating rate of 5° C./minute. During the second temperature rise, the variation in the difference in power absorbed by the empty crucible and by the crucible containing the sample of wax is measured as a function of the temperature. The melting point of the compound is the value of the temperature corresponding to the tip of the peak of the curve representing the variation in the difference in power absorbed as a function of the temperature.

The waxes capable of being used in a composition according to the invention are chosen from waxes of animal, vegetable, mineral or synthetic origin and their mixtures which are solid at ambient temperature. They can be hydrocarbon, fluorinated and/or silicone waxes.

Mention may in particular be made, by way of examples, of hydrocarbon waxes, such as natural beeswax (or bleached beeswax), synthetic beeswax, carnauba wax, rice bran wax, such as that sold under the reference NC 1720 by Cera Rica Noda, candelilla wax, such as that sold under the reference SP 75 G by Strahl & Pitsch, microcrystalline waxes, such as, for example, the microcrystalline waxes having a melting point of greater than 85° C., such as the products HI-MIC® 1070, 1080, 1090 and 3080 sold by Nippon Seiro, ceresins or ozokerites, such as, for example, isoparaffins having a melting point of less than 40° C., such as the product EMW-0003 sold by Nippon Seiro, α-olefin oligomers, such as the Performa V® 825, 103 and 260 polymers sold by New Phase Technologies, ethylene/propylene copolymers, such as Performalene® EP 700, polyethylene waxes (preferably with a molecular weight of between 400 and 600), Fischer-Tropsch waxes or the sunflower seed wax sold by Koster Keunen under the reference Sunflower Wax. Mention may also be made of silicone waxes, such as alkyl or alkoxy dimethicones having from 16 to 45 carbon atoms, or fluorinated waxes.

According to a specific embodiment, the wax used in a composition in accordance with the invention exhibits a melting point of greater than 35° C., better still of greater than 40° C., indeed even of greater than 45° C. or also of greater than 55° C.

According to a preferred embodiment, the wax or waxes are chosen from polymethylene waxes; the silicone wax sold under the name Dow Corning 2501 Cosmetic Wax by Dow Corning (INCI name: bis-PEG-18 methyl ether dimethyl silane); beeswax; vegetable waxes, such as carnauba wax; the mixture of polyglycerolated (3 mol) vegetable (mimosa/jojoba/sunflower) waxes sold under the name Hydracire S by Gattefosse; or the hydrogenated castor oil sold under the name Antisettle CVP by Cray Valley.

The other fatty substances which can be present in the fatty phase are, for example, fatty acids comprising from 8 to 30 carbon atoms, such as stearic acid, lauric acid or palmitic acid, or fatty alcohols comprising from 8 to 30 carbon atoms, such as stearyl alcohol, cetyl alcohol and their mixtures (cetearyl alcohol).

The fatty phase can also comprise other compounds dissolved in the oils, such as gelling agents and/or structuring agents.

These compounds can in particular be chosen from gums, such as silicone gums (dimethiconol); silicone resins, such as trifluoromethyl C1-4 alkyl dimethicone and trifluoropropyl dimethicone; and nonemulsifying silicone elastomers, such as the products sold under the KSG names by Shin-Etsu, under the Trefil name by Dow Corning or under the Gransil names by Grant Industries; and their mixtures.

These fatty substances can be chosen in a manner varied by a person skilled in the art in order to prepare a composition having the desired properties, for example of consistency or texture.

Aqueous Phase

When the composition in accordance with the invention is provided in the form of an emulsion, the aqueous phase comprises at least water. According to the formulation form of the composition, the amount of aqueous phase can range from 0.1% to 99% by weight, preferably from 0.5% to 98% by weight, better still from 30% to 95% by weight and even better still from 40% to 95% by weight, with respect to the total weight of the composition. This amount depends on the formulation form of the composition desired. The amount of water can represent all or a portion of the aqueous phase and it is generally at least 30% by weight, preferably at least 50% by weight and better still at least 60% by weight, with respect to the total weight of the composition.

The aqueous phase can comprise at least one hydrophilic solvent, such as, for example, substantially linear or branched lower monoalcohols having from 1 to 8 carbon atoms, such as ethanol, propanol, butanol, isopropanol or isobutanol; polyols, such as propylene glycol, isoprene glycol, butylene glycol, glycerol, sorbitol or polyethylene glycols and their derivatives, and their mixtures.

The emulsions generally comprise at least one additional emulsifier chosen from amphoteric, anionic, cationic or nonionic emulsifiers, used alone or as a mixture. The emulsifiers are appropriately chosen according to the emulsion to be obtained (W/O or O/W).

The additional emulsifiers are generally present in the composition in a proportion as active material (AM) ranging from 0.1% to 30% by weight and preferably from 0.2% to 20% by weight, with respect to the total weight of the composition.

Mention may be made, for the W/O emulsions, for example, as emulsifiers, of dimethicone copolyols, such as the mixture of cyclomethicone and of dimethicone copolyol sold under the name DC 5225 C by Dow Corning or the oxyethylenated polydimethylsiloxane PEG-10 Dimethicone sold under the name KF-6017 by Shin-Etsu, and alkyl dimethicone copolyols, such as the lauryl methicone copolyol sold under the name Dow Corning 5200 Formulation Aid by Dow Corning and the cetyl dimethicone copolyol sold under the name Abil EM 90® by Goldschmidt, or the polyglyceryl-4 isostearate/cetyl dimethicone copolyol/hexyl laurate mixture sold under the name Abil WE 09® by Goldschmidt. One or more coemulsifiers can also be added thereto. The coemulsifier can advantageously be chosen from the group consisting of polyol alkyl esters. Mention may in particular be made, as polyol alkyl esters, of glycerol and/or sorbitan esters, for example polyglyceryl isostearate, such as the product sold under the name Isolan GI 34 by Goldschmidt, sorbitan isostearate, such as the product sold under the name Arlacel 987 by ICI, sorbitan glyceryl isostearate, such as the product sold under the name Arlacel 986 by ICI, and their mixtures.

Mention may be made, for the O/W emulsions, for example, as emulsifiers, of nonionic surfactants and in particular esters of polyols and of fatty acid having a saturated or unsaturated chain comprising, for example, from 8 to 24 carbon atoms and better still from 12 to 22 carbon atoms, and their oxyalkylenated derivatives, that is to say derivatives comprising oxyethylene and/or oxypropylene units, such as glyceryl esters of $C_8$-$C_{24}$ fatty acid, and their oxyalkylenated derivatives; polyethylene glycol esters of $C_8$-$C_{24}$ fatty acid, and their oxyalkylenated derivatives; sorbitol esters of $C_8$-$C_{24}$ fatty acid, and their oxyalkylenated derivatives; fatty alcohol ethers; sugar ethers of $C_8$-$C_{24}$ fatty alcohols, and their mixtures.

Mention may in particular be made, as glyceryl ester of fatty acid, of glyceryl stearate (glyceryl mono-, di- and/or tristearate) (CTFA name: glyceryl stearate) or glyceryl ricinoleate, and their mixtures.

Mention may in particular be made, as polyethylene glycol ester of fatty acid, of polyethylene glycol stearate (polyethylene glycol mono-, di- and/or tristearate) and more especially polyethylene glycol 50 OE monostearate (CTFA name: PEG-50 stearate), polyethylene glycol 100 OE monostearate (CTFA name: PEG-100 stearate) and their mixtures.

Use may also be made of mixtures of these surfactants, such as, for example, the product comprising glyceryl stearate and PEG-100 stearate, sold under the name Arlacel 165 by Uniqema, and the product comprising glyceryl stearate (glyceryl mono/distearate) and potassium stearate, sold under the name Tegin by Goldschmidt (CTFA name: glyceryl stearate SE).

Mention may be made, as fatty alcohol ethers, for example, of polyethylene glycol ethers of fatty alcohol comprising from 8 to 30 carbon atoms and in particular from 10 to 22 carbon atoms, such as polyethylene glycol ethers of cetyl alcohol, stearyl alcohol or cetearyl alcohol (mixture of cetyl alcohol and stearyl alcohol). Mention may be made, for example, of ethers comprising from 1 to 200 and preferably from 2 to 100 oxyethylene groups, such as those with the CTFA name Ceteareth-20 or Ceteareth-30, and their mixtures.

Mention may be made, as examples of sugar mono- or polyalkyl esters or ethers, of methyl glucose isostearate, sold under the name Isolan-IS by Degussa Goldschmidt, or else sucrose distearate, sold under the name Crodesta F50 by Croda, and sucrose stearate, sold under the name Ryoto sugar ester S 1570 by Mitsubishi Kagaku Foods. Mention may also be made of lipoamino acids and their salts, such as monosodium and disodium acylglutamates, such as, for example, monosodium stearoyl glutamate, sold under the name Amisoft HS-11PF, and disodium stearoyl glutamate, sold under the name Amisoft HS-21P, by Ajinomoto.

In a known way, all the compositions of the invention can comprise one or more of the adjuvants normal in the cosmetic and dermatological fields: hydrophilic or lipophilic gelling agents and/or thickeners; moisturizers; emollients; hydrophilic or lipophilic active agents; agents for combating free radicals; sequestering agents; antioxidants; preservatives; basifying or acidifying agents; fragrances; film-forming agents; fillers; and their mixtures.

The amounts of these various adjuvants are those conventionally used in the fields under consideration. In particular, the amounts of active agents vary according to the desired objective and are those conventionally used in the fields under consideration, for example from 0.1% to 20% and preferably from 0.5% to 10% by weight of the total weight of the composition.

Active Agents

Mention may be made, by way of example of active agent and without implied limitation, of ascorbic acid and its derivatives, such as 5,6-di-O-dimethylsilylascorbate (sold by Exsymol under the reference PRO-AA), the potassium salt of D,L-α-tocopheryl 2-L-ascorbyl phosphate (sold by Senju Pharmaceutical under the reference Sepivital EPC), magnesium ascorbyl phosphate, sodium ascorbyl phosphate (sold by Roche under the reference Stay-C 50); phloroglucinol; enzymes; and their mixtures. According to a preferred embodiment of the invention, use is made, among oxidation-sensitive hydrophilic active agents, of ascorbic acid. The ascorbic acid can be of any nature. Thus, it can be of natural origin in the powder form or in the form of orange juice, preferably orange juice concentrate. It can also be of synthetic origin, preferably in the powder form.

Mention may be made, as other active agents which can be used in the composition of the invention, for example, of moisturizing agents, such as protein hydrolyzates and polyols, such as glycerol, glycols, such as polyethylene glycols; natural extracts; anti-inflammatories; procyanidol oligomers; vitamins, such as vitamin A (retinol), vitamin E (tocopherol), vitamin B5 (panthenol), vitamin B3 (niacinamide), the derivatives of these vitamins (in particular esters) and their mixtures; urea; caffeine; depigmenting agents, such as kojic acid, hydroquinone and caffeic acid; salicylic acid and its derivatives; -hydroxy acids, such as lactic acid and glycolic acid and their derivatives; retinoids, such as carotenoids and vitamin A derivatives; hydrocortisone; melatonin; extracts of algae, of fungi, of plants, of yeasts or of bacteria; steroids; antibacterial active agents, such as 2,4,4'-trichloro-2'-hydroxydiphenyl ether (or triclosan), 3,4,4'-trichlorocarbanilide (or triclocarban) and the acids indicated above, in particular salicylic acid and its derivatives; mattifying agents, such as fibers; tensioning agents; UV screening agents, in particular organic UV screening agents; and their mixtures.

According to an embodiment of the present invention, the composition includes the the Composition as claimed in claim 1 with the exception of the following composition:

|  | w/w | gm |
|---|---|---|
| Siloxane phase | | |
| Caprylyl methicone | 9.7% | 5 |
| Isododecane | 19.4% | 10 |
| Ethyl trisiloxane | 19.4% | 10 |
| Silica silylate | 1.5% | 0.763 |
| Siloxane emulsifiers | | |
| Lauryl polydimethylsiloxyethyl dimethicone crosspolymer | 3.9% | 2 |
| Lauryl PEG-9 polydimethylsiloxyethyl dimethicone | 3.9% | 2 |
| Aqueous phase | | |
| Propylene glycol | 4.9% | 2.5 |
| Butylene diglycol | 4.9% | 2.5 |
| Glycerol | 1.9% | 1 |
| Methyl propanediol | 7.8% | 4 |
| Deionised water | 19.4% | 10 |
| Phenoxyethanol (and) methyl isothiazolinone | 0.5% | 0.27 |
| CI 61570 | 0.6% | 0.3 |
| Granpowder nylon | 2.1% | 1.1 |

Of course, a person skilled in the art will take care to choose the optional adjuvant or adjuvants added to the composition according to the invention so that the advantageous properties intrinsically attached to the composition in accordance with the invention are not, or not substantially, detrimentally affected by the envisaged addition.

The examples which follow will make possible a better understanding of the invention without, however, exhibiting a limiting nature. The amounts indicated are given as % by weight of starting material, unless otherwise mentioned. The names of the compounds are shown as INCI names.

EXAMPLES

The residual greasy film is evaluated by a panel of 8 experts trained in the description of care products. The sensory evaluation is carried out as follows: 0.05 ml of product is applied to the back of the hand and the feel of the skin is evaluated at the end of application and 2 minutes after application.

The residual greasy film was recorded on a scale: Not/Medium/High

Anti-Aging Creams

The following compositions were prepared.

|   |   | A (comparative) | B (invention) |
|---|---|---|---|
| A | Dimethicone (and) Dimethicone/PEG-10/15 crosspolymer (KSG-210 from Shin-Etsu comprising 27% of AM) | 16.64 (4.5 AM) | 16.64 (4.5 AM) |
|   | Hydrogenated polyisobutene | 7 | 7 |
|   | Cyclohexasiloxane | 7.5 | 7.5 |
|   | Synthetic wax | 2 | 2 |
| B | Preservatives | 0.15 | 0.15 |
|   | Magnesium sulfate | 0.7 | 0.7 |
|   | Water | q.s. for 100 g | q.s. for 100 g |
|   | Glycerin | 7 | 7 |
| C | Aluminum Starch Octenylsuccinate (Dry Flow from Akzo Nobel) | 2 | 2 |
| D | Silica Silylate (Aerogel VM2270 from Dow Corning) | — | 1 |

AM: Active Material

Method of Preparation

Phases A and B are prepared by homogenization under hot conditions (70° C.) with gentle stirring. Emulsification is carried out by dispersion of phase B in phase A with stirring of Moritz type. Cooling is carried out with slow stirring and phases C and D are added at ambient temperature.

Results of the Comparative Evaluation

|   | A (comparative) | B (invention) |
|---|---|---|
| Residual film | 7/8 judged the film to be Medium 1/8 of the experts recorded the residual film as High | 8/8 of the experts considered that this product did Not leave a residual greasy film |

The composition B in accordance with the invention does not leave a residual greasy film, in contrast to the comparative composition A which does not comprise silica aerogel.

Examples: Moisturizing W/O Creams
The following compositions were prepared.

|   |   | C (comparative) | D (invention) |
|---|---|---|---|
| A | Dimethicone (and) Dimethicone/PEG-10/15 crosspolymer (KSG-210 from Shin-Etsu comprising 27% of AM) | 3.6 | 3.6 |
|   | PEG-10 dimethicone (KF 6017 from Shin-Etsu) | 0.5 | 0.5 |
|   | Cyclohexasiloxane | 5.5 | 5.5 |
|   | Synthetic wax | 2 | 2 |
|   | Preservatives | 0.75 | 0.75 |
|   | Isohexadecane | 6 | 6 |
| B | Disodium EDTA | 0.15 | 0.15 |
|   | Sodium polyacrylate (Cosmedia SP from Cognis) | 1 | 1 |
|   | Water | q.s. for 100 g | q.s. for 100 g |
|   | Glycerin | 7 | 7 |
| C | Disteardimonium hectorite (Bentone 38VCG from Elementis) | 0.6 | 0.6 |
| D | Propylene carbonate | 0.16 | 0.16 |
| E | Methylsilanol/silicate crosspolymer (NLK 506 from Takemoto) | 3 | 3 |
|   | Silica Silylate (Aerogel VM2270 from Dow Corning) | — | 1 |

Method of Preparation

Phases A, B and C are prepared by homogenization under hot conditions (70° C.) with stirring. Emulsification is carried out by dispersion of phase B in phase A with stirring of Moritz type, followed by addition of phase C. Cooling is carried out with slow stirring and addition of the fillers (phase D) at ambient temperature.

Results of the Comparative Evaluation

|   | C (comparative) | D (invention) |
|---|---|---|
| Residual film | 7/8 judged the film to be Medium 1 expert (having dry skin) judged that the product did Not leave a residual film | 8/8 of the experts considered that this product did Not leave a residual greasy film |

The composition D in accordance with the invention does not leave a residual greasy film, in contrast to the comparative composition C which does not comprise silica aerogel.

The invention claimed is:

1. A composition for topical application provided in the form of a water-in-oil emulsion or in the form of an oil-in-water emulsion comprising:
   hydrophobic silica aerogel particles exhibiting a specific surface per unit of weight ($S_W$) ranging from 500 to 1500 m$^2$/g, and a size, expressed as volume-average diameter (D[0.5]), ranging from 1 to 1500 μm; and
   at least one emulsifying silicone elastomer; wherein said at least one emulsifying silicone elastomer is a polyoxyalkylenated silicone elastomer.

2. Composition as claimed in claim 1 with the exception of the following composition:

|   | w/w | gm |
|---|---|---|
| Siloxane phase |   |   |
| Caprylyl methicone | 9.7% | 5 |
| Isododecane | 19.4% | 10 |

-continued

|  | w/w | gm |
| --- | --- | --- |
| Ethyl trisiloxane | 19.4% | 10 |
| Silica silylate | 1.5% | 0.763 |
| Siloxane emulsifiers |  |  |
| Lauryl polydimethylsiloxyethyl dimethicone crosspolymer | 3.9% | 2 |
| Lauryl PEG-9 polydimethylsiloxyethyl dimethicone | 3.9% | 2 |
| Aqueous phase |  |  |
| Propylene glycol | 4.9% | 2.5 |
| Butylene diglycol | 4.9% | 2.5 |
| Glycerol | 1.9% | 1 |
| Methyl propanediol | 7.8% | 4 |
| Deionised water | 19.4% | 10 |
| Phenoxyethanol (and) methyl isothiazolinone | 0.5% | 0.27 |
| CI 61570 | 0.6% | 0.3 |
| Granpowder nylon | 2.1% | 1.1. |

3. The composition as claimed in claim 1, in which the hydrophobic silica aerogel particles exhibit a specific surface per unit of volume $S_V$ ranging from 5 to 60 m²/cm³ and/or an oil absorption capacity, measured at the wet point, ranging from 5 to 18 ml/g of particles.

4. The composition as claimed in claim 1, in which the hydrophobic silica aerogel particles are trimethylsiloxylated silica particles.

5. The composition as claimed in claim 1, in which the hydrophobic silica aerogel particles are present in a content as active material ranging from 0.1% to 15% by weight with respect to the total weight of the composition.

6. The composition as claimed in claim 1, in which the silicone elastomer or elastomers comprising at least one oxyalkylene chain are obtained by an addition and cross-linking reaction of a diorganosiloxane comprising at least one hydrogen bonded to silicon and a polyoxyalkylene having at least two ethylenically unsaturated groups, in the presence of a catalyst.

7. The composition as claimed in claim 1, in which the emulsifying silicone elastomer or elastomers are present in a content as active material ranging from 0.05% to 10% by weight with respect to the total weight of said composition.

8. The composition as claimed in claim 1, which is provided in the form of an emulsion of water-in-oil type (inverse emulsion).

9. A method for the cosmetic treatment of a keratinous substance, in which a cosmetic composition as defined in claim 1 is applied to the keratinous sub stance.

10. A method for the cosmetic or dermatological for caring for, protecting and/or making up the skin of the body or face or for caring for the hair in which a cosmetic composition as defined in claim 1 is applied to the skin or hair.

11. The composition as claimed in claim 1, wherein the hydrophobic silica aerogel particles exhibit a specific surface per unit of weight ($S_W$) ranging from 600 to 800 m²/g, and a size, expressed as volume-average diameter (D[0.5]), ranging from 5 to 15 μm.

12. The composition as claimed in claim 2, in which the hydrophobic silica aerogel particles exhibit a specific surface per unit of volume $S_V$ ranging from 5 to 60 m²/cm³ and/or an oil absorption capacity, measured at the wet point, ranging from 5 to 18 ml/g of particles.

13. The composition as claimed in claim 2, in which the hydrophobic silica aerogel particles are trimethylsiloxylated silica particles.

14. The composition as claimed in claim 3, in which the hydrophobic silica aerogel particles are trimethylsiloxylated silica particles.

15. The composition as claimed in claim 2, in which the hydrophobic silica aerogel particles are present in a content as active material ranging from 0.1% to 15% by weight.

16. The composition as claimed in claim 3, in which the hydrophobic silica aerogel particles are present in a content as active material ranging from 0.1% to 15% by weight.

17. The composition as claimed in claim 4, in which the hydrophobic silica aerogel particles are present in a content as active material ranging from 0.1% to 15% by weight.

18. The composition as claimed in claim 1, in which the hydrophobic silica aerogel particles are present in a content as active material ranging from 1% to 10% by weight.

* * * * *